(12) United States Patent
Ruchti et al.

(10) Patent No.: US 8,771,251 B2
(45) Date of Patent: Jul. 8, 2014

(54) SYSTEMS AND METHODS FOR MANAGING AND DELIVERING PATIENT THERAPY THROUGH ELECTRONIC DRUG DELIVERY SYSTEMS

(75) Inventors: Timothy Lewis Ruchti, Gurnee, IL (US); Steven R. Wehba, Carlsbad, CA (US); John Harrison Thornley, Charlotte, NC (US); Harsh Dharwad, San Diego, CA (US); Joanne Marie Watt, Tower Lakes, IL (US); Carol Dian Martin, Charlotte, NC (US); Suzanne Willey, San Diego, CA (US)

(73) Assignee: Hospira, Inc., Lake Forest, IL (US)

( * ) Notice: Subject to any disclaimer, the term of this patent is extended or adjusted under 35 U.S.C. 154(b) by 392 days.

(21) Appl. No.: 12/970,777

(22) Filed: Dec. 16, 2010

(65) Prior Publication Data

US 2011/0152830 A1 Jun. 23, 2011

Related U.S. Application Data

(60) Provisional application No. 61/287,579, filed on Dec. 17, 2009.

(51) Int. Cl.
*A61M 31/00* (2006.01)
*G06F 19/00* (2011.01)

(52) U.S. Cl.
CPC ........ *G06F 19/3468* (2013.01); *G06F 19/3437* (2013.01); *A61M 2205/3576* (2013.01); *A61M 2205/3561* (2013.01); *A61M 2205/3507* (2013.01); *A61M 2205/3546* (2013.01); *A61M 2205/35* (2013.01)
USPC ........................................... 604/504; 604/67

(58) Field of Classification Search
USPC ............ 604/504, 503, 890.1, 65–67; 702/2, 3
See application file for complete search history.

(56) References Cited

U.S. PATENT DOCUMENTS

| 4,055,175 A | 10/1977 | Clemens et al. |
|---|---|---|
| 4,151,845 A | 5/1979 | Clemens |

(Continued)

FOREIGN PATENT DOCUMENTS

| DE | 3112762 A1 | 1/1983 |
|---|---|---|
| DE | 3435647 A1 | 7/1985 |

(Continued)

OTHER PUBLICATIONS

B. Wayne Bequette, Ph.D., Analysis of Algorithms for Intensive Care Unit Blood Glucose Control, Jrnl. Of Diabetes Science & Technology, Nov. 1, 2007, vol. 1, Issue 6, USA.

(Continued)

*Primary Examiner* — Aarti B Berdichevsky
*Assistant Examiner* — Bradley Osinski
(74) *Attorney, Agent, or Firm* — Michael R. Crabb

(57) ABSTRACT

In example methods and systems described, a medical device can store information locally and in a separate database on a server, for example. If the device fails, or a patient is moved to a second device, information may be transferred to the second device such that the second device can resume a complex therapy at a point where the initial medical device left off. The data necessary to restart the complex therapy system may include certain underlying patient-specific parameters according to a model capturing the patient's physiological response to the medication in question. As a result, it is not necessary for the second device to restart the complex therapy or regress to an initial set of baseline assumptions.

19 Claims, 8 Drawing Sheets

(56) References Cited

U.S. PATENT DOCUMENTS

| | | |
|---|---|---|
| 4,240,438 A | 12/1980 | Updike |
| 4,308,866 A | 1/1982 | Jelliffe |
| 4,370,983 A | 2/1983 | Lichtenstein |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,559,037 A | 12/1985 | Franetzki et al. |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,676,776 A | 6/1987 | Howson |
| 4,679,562 A | 7/1987 | Luksha |
| 4,685,903 A | 8/1987 | Cable et al. |
| 4,696,671 A | 9/1987 | Epstein et al. |
| 4,714,462 A | 12/1987 | DiDomenico |
| 4,722,734 A | 2/1988 | Kolln |
| 4,731,051 A | 3/1988 | Fischell |
| 4,741,732 A | 5/1988 | Crankshaw et al. |
| 4,756,706 A | 7/1988 | Kerns |
| 4,776,842 A | 10/1988 | Franetzki et al. |
| 4,838,856 A | 6/1989 | Mulreany et al. |
| 4,838,857 A | 6/1989 | Strowe et al. |
| 4,898,578 A | 2/1990 | Rubalcaba, Jr. |
| 4,943,279 A | 7/1990 | Samiotes et al. |
| 5,000,739 A | 3/1991 | Kulisz et al. |
| 5,010,473 A | 4/1991 | Jacobs |
| 5,034,004 A | 7/1991 | Crankshaw |
| 5,041,086 A | 8/1991 | Koenig et al. |
| 5,078,683 A | 1/1992 | Sancoff et al. |
| 5,084,828 A | 1/1992 | Kaufman et al. |
| 5,100,380 A | 3/1992 | Epstein et al. |
| 5,104,374 A | 4/1992 | Bishko et al. |
| 5,109,850 A | 5/1992 | Blanco et al. |
| 5,131,816 A | 7/1992 | Brown |
| 5,153,827 A | 10/1992 | Coutre et al. |
| 5,181,910 A | 1/1993 | Scanlon |
| 5,190,522 A | 3/1993 | Wocicki et al. |
| 5,216,597 A | 6/1993 | Beckers |
| 5,221,268 A | 6/1993 | Barton et al. |
| 5,243,982 A | 9/1993 | Mostl et al. |
| 5,244,463 A | 9/1993 | Cordner, Jr. et al. |
| 5,256,156 A | 10/1993 | Kern et al. |
| 5,256,157 A | 10/1993 | Samiotes et al. |
| 5,317,506 A | 5/1994 | Coutre et al. |
| 5,330,634 A | 7/1994 | Wong et al. |
| 5,338,157 A | 8/1994 | Blomquist |
| 5,364,346 A | 11/1994 | Schrezenmeir |
| 5,368,562 A | 11/1994 | Blomquist et al. |
| 5,376,070 A | 12/1994 | Purvis et al. |
| 5,389,071 A | 2/1995 | Kawahara et al. |
| 5,389,078 A | 2/1995 | Zalesky et al. |
| 5,423,748 A | 6/1995 | Uhala |
| 5,429,602 A | 7/1995 | Hauser |
| 5,485,408 A | 1/1996 | Blomquist |
| 5,505,828 A | 4/1996 | Wong et al. |
| 5,520,637 A | 5/1996 | Pager et al. |
| 5,643,212 A | 7/1997 | Coutre et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A * | 9/1997 | Sillen et al. .................. 604/503 |
| 5,681,285 A | 10/1997 | Ford et al. |
| 5,713,856 A | 2/1998 | Eggers et al. |
| 5,733,259 A | 3/1998 | Valcke et al. |
| 5,744,027 A | 4/1998 | Connell et al. |
| 5,772,635 A | 6/1998 | Dastur et al. |
| 5,781,442 A | 7/1998 | Engleson et al. |
| 5,782,805 A | 7/1998 | Meinzer et al. |
| 5,788,669 A | 8/1998 | Peterson |
| 5,822,715 A | 10/1998 | Worthington et al. |
| 5,885,245 A | 3/1999 | Lynch et al. |
| 5,910,252 A | 6/1999 | Truitt et al. |
| 5,935,099 A | 8/1999 | Peterson et al. |
| 5,941,846 A | 8/1999 | Duffy et al. |
| 5,956,501 A | 9/1999 | Brown |
| 6,000,828 A | 12/1999 | Leet |
| 6,122,536 A | 9/2000 | Sun et al. |
| 6,517,482 B1 | 2/2003 | Elden et al. |
| 6,540,672 B1 * | 4/2003 | Simonsen et al. ............ 600/300 |
| 6,544,212 B2 | 4/2003 | Galley et al. |
| 6,558,351 B1 | 5/2003 | Steil et al. |
| 6,565,509 B1 | 5/2003 | Say et al. |
| 6,572,542 B1 | 6/2003 | Houben et al. |
| 6,572,545 B2 | 6/2003 | Knobbe et al. |
| 6,599,281 B1 | 7/2003 | Struys et al. |
| 6,605,072 B2 | 8/2003 | Struys et al. |
| 6,689,091 B2 | 2/2004 | Bui et al. |
| 6,721,582 B2 | 4/2004 | Trepagnier et al. |
| 6,740,072 B2 | 5/2004 | Starkweather et al. |
| 6,780,156 B2 | 8/2004 | Haueter et al. |
| 6,852,104 B2 | 2/2005 | Blomquist |
| 6,885,881 B2 | 4/2005 | Leonhardt |
| 6,915,170 B2 | 7/2005 | Engleson et al. |
| 6,923,763 B1 | 8/2005 | Kovatchev et al. |
| 6,936,029 B2 | 8/2005 | Mann et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,985,870 B2 | 1/2006 | Martucci et al. |
| 6,997,920 B2 | 2/2006 | Mann et al. |
| 7,025,743 B2 | 4/2006 | Mann et al. |
| 7,029,455 B2 | 4/2006 | Flaherty |
| 7,060,059 B2 | 6/2006 | Keith et al. |
| 7,108,680 B2 | 9/2006 | Rohr et al. |
| 7,109,878 B2 | 9/2006 | Mann et al. |
| 7,137,964 B2 | 11/2006 | Flaherty |
| 7,171,277 B2 | 1/2007 | Engleson et al. |
| 7,201,734 B2 | 4/2007 | Hickle |
| 7,204,823 B2 | 4/2007 | Estes et al. |
| 7,220,240 B2 | 5/2007 | Struys et al. |
| 7,229,430 B2 | 6/2007 | Hickle et al. |
| 7,238,164 B2 | 7/2007 | Childers et al. |
| 7,247,154 B2 | 7/2007 | Hickle |
| 7,267,665 B2 | 9/2007 | Steil et al. |
| 7,278,983 B2 | 10/2007 | Ireland et al. |
| 7,347,836 B2 | 3/2008 | Peterson et al. |
| 7,354,420 B2 | 4/2008 | Steil et al. |
| 7,399,277 B2 | 7/2008 | Saidara et al. |
| 7,402,153 B2 | 7/2008 | Steil et al. |
| 7,483,756 B2 | 1/2009 | Engleson et al. |
| 7,491,187 B2 | 2/2009 | Van Den Berghe et al. |
| 2002/0038392 A1 | 3/2002 | De la Huerga |
| 2002/0040208 A1 | 4/2002 | Flaherty et al. |
| 2003/0079746 A1 | 5/2003 | Hickle |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0140928 A1 | 7/2003 | Bui |
| 2003/0141981 A1 | 7/2003 | Bui |
| 2003/0143746 A1 | 7/2003 | Sage, Jr. |
| 2003/0212364 A1 | 11/2003 | Mann et al. |
| 2003/0212379 A1 | 11/2003 | Bylund et al. |
| 2004/0147034 A1 | 7/2004 | Gore et al. |
| 2004/0167464 A1 | 8/2004 | Ireland et al. |
| 2004/0193453 A1 | 9/2004 | Butterfield |
| 2004/0204673 A1 | 10/2004 | Flaherty et al. |
| 2004/0220517 A1 | 11/2004 | Starkweather et al. |
| 2004/0254434 A1 | 12/2004 | Goodnow et al. |
| 2005/0021006 A1 | 1/2005 | Tonnies |
| 2005/0065465 A1 | 3/2005 | Lebel |
| 2005/0119914 A1 | 6/2005 | Batch |
| 2005/0137522 A1 | 6/2005 | Aoki |
| 2005/0171503 A1 * | 8/2005 | Van Den Berghe et al. .. 604/504 |

(56) References Cited

U.S. PATENT DOCUMENTS

| | | |
|---|---|---|
| 2005/0177096 A1 | 8/2005 | Bollish |
| 2005/0182306 A1 | 8/2005 | Sloan |
| 2005/0182355 A1 | 8/2005 | Bui |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2006/0009727 A1 | 1/2006 | O'Mahony et al. |
| 2006/0009734 A1 | 1/2006 | Martin |
| 2006/0026205 A1 | 2/2006 | Butterfield |
| 2006/0047270 A1 | 3/2006 | Shelton |
| 2006/0047538 A1 | 3/2006 | Condurso |
| 2006/0053036 A1 | 3/2006 | Coffman |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers |
| 2006/0173260 A1 | 8/2006 | Gaoni et al. |
| 2006/0173406 A1 | 8/2006 | Hayes et al. |
| 2006/0190302 A1 | 8/2006 | Eggers |
| 2006/0195022 A1 | 8/2006 | Trepagnier et al. |
| 2006/0224141 A1 | 10/2006 | Rush et al. |
| 2006/0229551 A1 | 10/2006 | Martinez |
| 2006/0264895 A1 | 11/2006 | Flanders |
| 2007/0015972 A1 | 1/2007 | Wang |
| 2007/0058412 A1 | 3/2007 | Wang et al. |
| 2007/0060796 A1 | 3/2007 | Kim |
| 2007/0060871 A1 | 3/2007 | Istoc |
| 2007/0065363 A1 | 3/2007 | Dalal et al. |
| 2007/0078314 A1 | 4/2007 | Grounsell |
| 2007/0088333 A1 | 4/2007 | Levin et al. |
| 2007/0112298 A1 | 5/2007 | Mueller et al. |
| 2007/0118405 A1 | 5/2007 | Campbell et al. |
| 2007/0142822 A1 | 6/2007 | Remde |
| 2007/0191817 A1 | 8/2007 | Martin |
| 2007/0215545 A1 | 9/2007 | Bissler et al. |
| 2007/0299389 A1 | 12/2007 | Halbert |
| 2008/0097289 A1 | 4/2008 | Steil et al. |
| 2008/0139907 A1 | 6/2008 | Rao et al. |
| 2008/0214919 A1 | 9/2008 | Harmon et al. |
| 2008/0262469 A1 | 10/2008 | Bristol et al. |
| 2008/0300572 A1 | 12/2008 | Rankers et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0054754 A1 | 2/2009 | McMahon et al. |
| 2009/0209938 A1 | 8/2009 | Aalto-Setala |
| 2009/0221890 A1 | 9/2009 | Saffer et al. |
| 2010/0036310 A1* | 2/2010 | Hillman ............ 604/20 |
| 2010/0121170 A1 | 5/2010 | Rule |

FOREIGN PATENT DOCUMENTS

| | | |
|---|---|---|
| DE | 19844252 A1 | 9/1998 |
| DE | 10352456 A1 | 7/2005 |
| WO | 9116416 A1 | 10/1991 |
| WO | 0013580 A1 | 3/2000 |
| WO | 03006091 A1 | 1/2003 |

OTHER PUBLICATIONS

Philip Goldberg, et al., Critical Results of an Updated Insulin Infusion Protocol in Critically Ill Patients, Diabetes Spectrum, 2005, vol. 18, No. 3, USA.

Daniel Sebald and Timothy Ruchti, Numerical Analysis of Comprehensive In Silico Subcutaneous Insulin Absorption Compartment Model, 31st Annual International Conference of the IEEE EMBS, Sep. 2-6, 2009, Minnesota, MN, USA.

American College of Endocrinology Position Statement on Inpatient Diabetes and Metabolic Control, Endocrine Practice, Jan./Feb. 2004, p. 77-82, vol. 10, No. 1, USA.

Michael Simonsen, Ph.D., POC Testing, New Monitoring Strategies on Fast Growth Paths in European Healthcare Arenas, Biomedical Business & Technology, Jan. 2007, p. 2-8, vol. 30, No. 1, USA.

Neil Halpern, et al., Changes in Critical Care Beds and Occupancy in the United States 1985-2000: Differences attributable to hospital size, Critical Care Med., 2006, p. 2105-2112, vol. 34, No. 8, USA.

G. Van Den Berghe, et al., Intensive Insulin Therapy in Critically Ill Patients, New England Journal of Medicine (NEJM), 2001, p. 1359-67, vol. 345, No. 19, USA.

G. Van Den Berghe, et al., Intensive Insulin Therapy in the Medical ICU, New England Journal of Medicine (NEJM) 2006, p. 449-61, vol. 354, No. 5, USA.

Daleen Aragon, RN, Ph.D., CCRN, Evaluation of Nursing Work Effort and Perceptions About Blood Glucose Testing in Tight Glycemic Control, American Journal of Critical Care, Jul. 1, 2006, p. 370-377, vol. 15, No. 4, USA.

L. Saager, et al., Computer-Guided Versus Standard Protocol for Insulin Administration in Diabetic Patients Undergoing Cardiac Surgery, Annual Meeting of the American Society of Critical Care Anesthesiologists Oct. 13, 2006, USA.

Paul C. Davidson MD et al., Glucommander—A computer-directed intravenous insulin system shown to be safe, simple, and effective in 120,618h of operation, Diabetes Care, Oct. 1, 2005, vol. 28, No. 10, USA.

B. Wayne Bequette, Ph.D., A Critical Assessment of Algorithms and Challenges in the Development of a Closed-Loop Artificial Pancreas, Diabetes Technology & Therapeutics, 2005, p. 28-48, vol. 7, No. 1, USA.

Eric J. Fogt, et al., Development and Evaluation of a Glucose Analyzer for a Glucose-Controlled Insulin Infusion System (Biostator®), Clinical Chemistry, 1978, p. 1366-1372, vol. 24, No. 8, USA.

Diabetes Close Up, Close Concerns AACE Inpatient Management Conference Report, Consensus Development Conference on Inpatient Diabetes and Metabolic Control, Washington, D.C. Dec. 14-16, 2003, p. 1-32, USA.

Etie Moghissi, MD, FACP, FACE, Hyperglycemia in Hospitalized Patients—A Challenge and an Opportunity to Improve Care of Patients With Diabetes, Suppl. to ACP Hospitalist, Jun. 15, 2008, p. 2-28, USA.

\* cited by examiner

SYSTEMS AND METHODS FOR MANAGING AND DELIVERING PATIENT THERAPY THROUGH ELECTRONIC DRUG DELIVERY SYSTEMS

CROSS-REFERENCE TO RELATED APPLICATIONS

This application is a nonprovisional of U.S. Provisional Patent Application Ser. No. 61/287,579, filed Dec. 17, 2009, having the title "Systems and Methods for Managing and Delivering Patient Therapy through Electronic Drug Delivery Systems," the entirety of which is hereby incorporated by reference.

FIELD

The present application relates to automation of a drug therapy, and more particularly, to systems and methods for managing and delivering patient therapy through electronic drug delivery systems, which include an infusion pump and a sensor, monitor, or meter for measuring a patient physiological characteristic or response to the therapy, for example.

BACKGROUND

Treatment of hospitalized patients frequently involves control of one or more physiological parameters in concert with administration of fluids, pharmaceuticals, and nutrition through intravenous (IV) infusion pumps. Current systems rely on intervention by clinicians who manually adjust infusion rates on the basis of monitored variables and "paper" protocols, which are derived from experience and/or evidence as may be presented through medical literature.

However, a manual control (or titration) process is burdensome to care providers and may not achieve optimal care for a patient. In part, this is due to complexity of the physiological control problem, limited resources available to monitor patient status, and the static nature of adjustment protocols. Manual intervention also provides opportunities for introduction of medication errors during calculation, data entry, or IV pump programming, for example. In addition, paper protocols and/or nomograms used by a bedside nurse may be necessarily simple and may be unable to compensate for a wide variety of patient drug sensitivities, nonlinear drug response characteristics, and dynamic nature through time.

As one example of a condition that requires treatment possibly using manual intervention, hyperglycemia or high blood sugar is a condition in which an excessive amount of glucose circulates in blood plasma. Pronounced hyperglycemia occurs in approximately 75% of acutely ill patients and is associated with a significant increase in morbidity and mortality. Studies have shown that maintaining normal blood glucose levels through intravenous (IV) infusion of insulin can lead to improved outcomes in acutely ill patients. Thus, treatment of hyperglycemia requires elimination of an underlying cause if possible, e.g., treatment of diabetes when diabetes is the cause, and in most cases, direct administration of insulin is used, under medical supervision. However, current clinical practices for treating hyperglycemia that involve intensive insulin therapy are a burdensome activity that involve frequent (1-2 hour) blood glucose measurements followed by manual adjustment of an IV insulin infusion rate. Changes to insulin infusion are directed by protocols that can fail to adequately represent patient-to-patient differences and present a high risk of hypoglycemia. Thus, manual supervision by medical personnel can increase chances of human error and often does not consider specific patient responses to a drug therapy.

SUMMARY

In example methods described herein, a method for managing and delivering patient therapy through electronic drug delivery systems, which may include an infusion pump and a sensor, monitor, or meter for measuring a patient physiological characteristic or response to the therapy, is provided. The method includes a first drug delivery system that is connected to a patient receiving a patient identifier that corresponds to the patient, and the first drug delivery system estimating underlying patient-specific control variables based on (i) a therapy provided for a patient and (ii) an observed patient-specific response to the therapy. Based on (i) the estimated underlying patient-specific control variables, (i) the observed patient-specific response to the therapy, and (iii) a therapy objective, the first drug delivery system provides an updated therapy for the patient. The method further includes the first drug delivery system transferring to a remote system, which may include one or more computers, interfaces and databases, a record of the updated therapy provided for the patient and the estimated underlying patient-specific control variables. Upon connecting a second drug delivery system to the patient, the second drug delivery system receives the patient identifier, and the second drug delivery system communicates with the remote system to access the record of the updated therapy and the estimated underlying patient-specific control variables associated with the patient identifier.

Using example methods described below, the second drug delivery system receives the record of therapy and the estimated underlying patient-specific control variables associated with the patient identifier from the remote system, and continues the therapy for the patient at a point where the therapy was previously reported or optionally discontinued by the first drug delivery system.

In other aspects, example systems described herein provide for managing and delivering patient therapy through drug delivery systems. The system includes a first drug delivery system connected to a patient that receives a patient identifier that corresponds to the patient, and based on (i) estimated underlying patient-specific control variables, (i) an observed patient-specific response to the therapy, and (iii) a therapy objective, the first drug delivery system provides an updated therapy for the patient. The first drug delivery system transfers to a remote system a record of the updated therapy provided for the patient and the estimated underlying patient-specific control variables. The system also includes a second drug delivery system that receives the patient identifier and communicates with the remote system to access the record of the updated therapy and the estimated underlying patient-specific control variables associated with the patient identifier.

In still other aspects, a computer readable medium having stored therein instructions executable by a computing device to cause the computing device to perform certain functions is provided. The functions include receiving from a first electronic drug delivery system a record of estimated underlying patient-specific control variables for a patient. The underlying patient-specific control variables are based on (i) a therapy provided for a patient and (ii) an observed patient-specific response to the therapy. The functions also include receiving from the first electronic drug delivery system an updated therapy provided for the patient. The updated therapy being based on (i) the estimated underlying patient-specific control variables, (i) the observed patient-specific response to the therapy, and (iii) a therapy objective. The functions also include transferring to a second electronic drug delivery system a record of the updated therapy provided for the patient and the estimated underlying patient-specific control variables associated with the patient.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
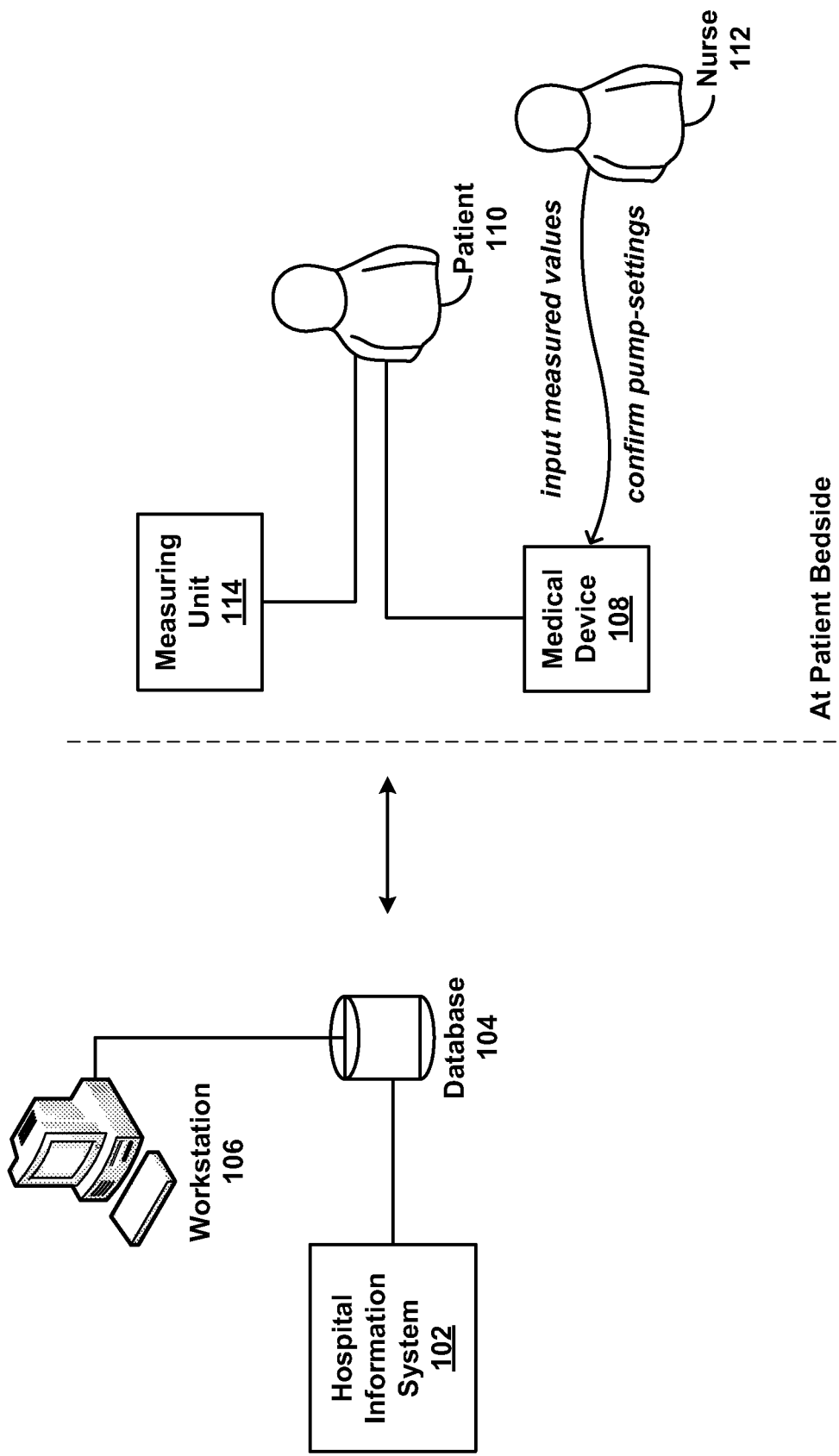
FIG. 1 illustrates an example configuration for managing and delivering patient therapy through drug delivery systems.

In the following detailed description, reference is made to the accompanying drawings, which form a part hereof. In the drawings, similar symbols typically identify similar components, unless context dictates otherwise. Illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

Automation of a therapy through systems, such as an infusion system, provides opportunities to improve workflow, reduce user error, and enable a desired therapy outcome. For example, an infusion protocol algorithm can be included on an infusion pump for further automation of the system to reduce input errors, improve workflow, and improve efficiency. In addition, infusion, testing, and monitoring devices can be networked together with servers and other computers in a hospital setting to enable information to be transferred to the devices. Such information includes medication information, medication rates, volume to be infused, duration, frequency, caregiver, device and patient identifiers, monitored values, and point-of-care test data, for example.

In example methods and systems described, a medical device can store information locally and in a separate database on a server, for example. If the device fails, or a patient is moved to a second device, information may be transferred to the second device such that the second device can resume a complex therapy at a point where the initial medical device left off. The data necessary to restart the complex (e.g., iterative or recursive) therapy system may include certain calculated or estimated underlying patient-specific control variables or parameters according to a model capturing the patient's physiological response to the medication in question. As a result, it is possible for the second device to start the complex therapy at any point on a timeline where the first device was modeling or learning about the patient response and to use that information rather than having to restart the second device on the complex therapy from an initial set of baseline assumptions. Alternatively, a portion of or the entire cumulative history of the therapy from the first device can be transferred or transmitted to the second device and the patient-specific control variables can be recalculated by the second device using the historical information.

Referring now to the figures, FIG. 1 illustrates an example configuration for managing and delivering patient therapy through electronic drug delivery systems. A hospital information system 102 is provided to support admission, discharge, and transfer of patient data throughout a hospital or medical community, for example. The hospital information system 102 may be in the form of a server or other type of workstation, and may be connected to a database 104 via a network or other interface, for example. The database 104 may include patient-specific information relating to treatment for the patient. A workstation 106 may also be connected to the database 104 for use by a hospital administrator or nurse to input patient data, and to provide the ability to generate reports, generate and print subcutaneous insulin dosing orders, and modify configuration parameters, for example. The hospital information system 102, the database 104, and the workstation 106 may be located in a hospital or off-site as well.

A medical device 108 located at a patient's bedside may be in communication with the hospital information system 102, the database 104, or the workstation 106 using a network with either a wireless or wired connection to receive patient-specific data, which may include data from an Admission Discharge Transfer, a Pharmacy Information System, or Laboratory Information Systems, and to deliver patient therapy to a patient 110. A nurse 112 or other hospital personnel may input settings to the medical device 108 to delivery therapy to the patient 110 to whom the medical device 108 is connected. A measuring unit 114 can be operatively connected to, associated with or used on the patient 110 to sense, monitor or measure a patient physiological characteristic or response to the therapy. Blood or another fluid can be withdrawn from the patient and remotely tested or analyzed by a measuring unit 114. For example, the measuring unit 114 may include a blood pressure monitor, a blood-glucose monitor, or other monitor/meter as needed to measure a desired characteristic of the patient 110.

In one example, the medical device 108 may be an infusion pump that controls a level of glucose in a patient using a software algorithm including a feedback mechanism for blood sugar control for stressed and critically ill patients. For example, the medical device 108 may be a Symbiq® infusion system, pump or infuser, available from Hospira, Inc. of Lake Forest, Ill., that runs software, such as EndoTool® also available from Hospira, Inc., to perform a method of calculating appropriate insulin doses/rates and glucose measurement intervals to provide intensive insulin therapy. The method may provide clinicians with insulin dosage, D50W dosage (Dextrose 50% in water), and testing frequency (time of next glucose test) recommendations through a pump interface, for example. After the clinician has confirmed or modified the recommended insulin infusion rate, the pump infusion rate can be automatically changed.

In addition to providing a recommended rate for insulin infusion, the medical device 108 may display a time for a next glucose measurement. The glucose measurement can be provided as described above or the measuring unit 114 may include a handheld glucometer carried by the clinician. The measuring unit 114 can be in communication with the medical device 108 via a hard-wired or wireless connection or the measuring unit 114 can provide the clinician with the measurements to manually enter into the pump. Clinicians can be reminded at designated times through the pump interface to update the patient's blood glucose level through the interface. A series of alerts and/or alarms are generated by the medical device 108 if a glucose measurement is not received in the designated time.

The medical device 108 may be capable of autonomous operation without connection to a server or any of the hospital information system 102, the database 104, or the workstation 106. However, the medical device 108 can be configured using the workstation 106 or by the nurse 112 using an interface on the medical device 108 to accept Clinical Care Area (CCA) specific and hospital specific configurations or other patient data.

Figure 2:
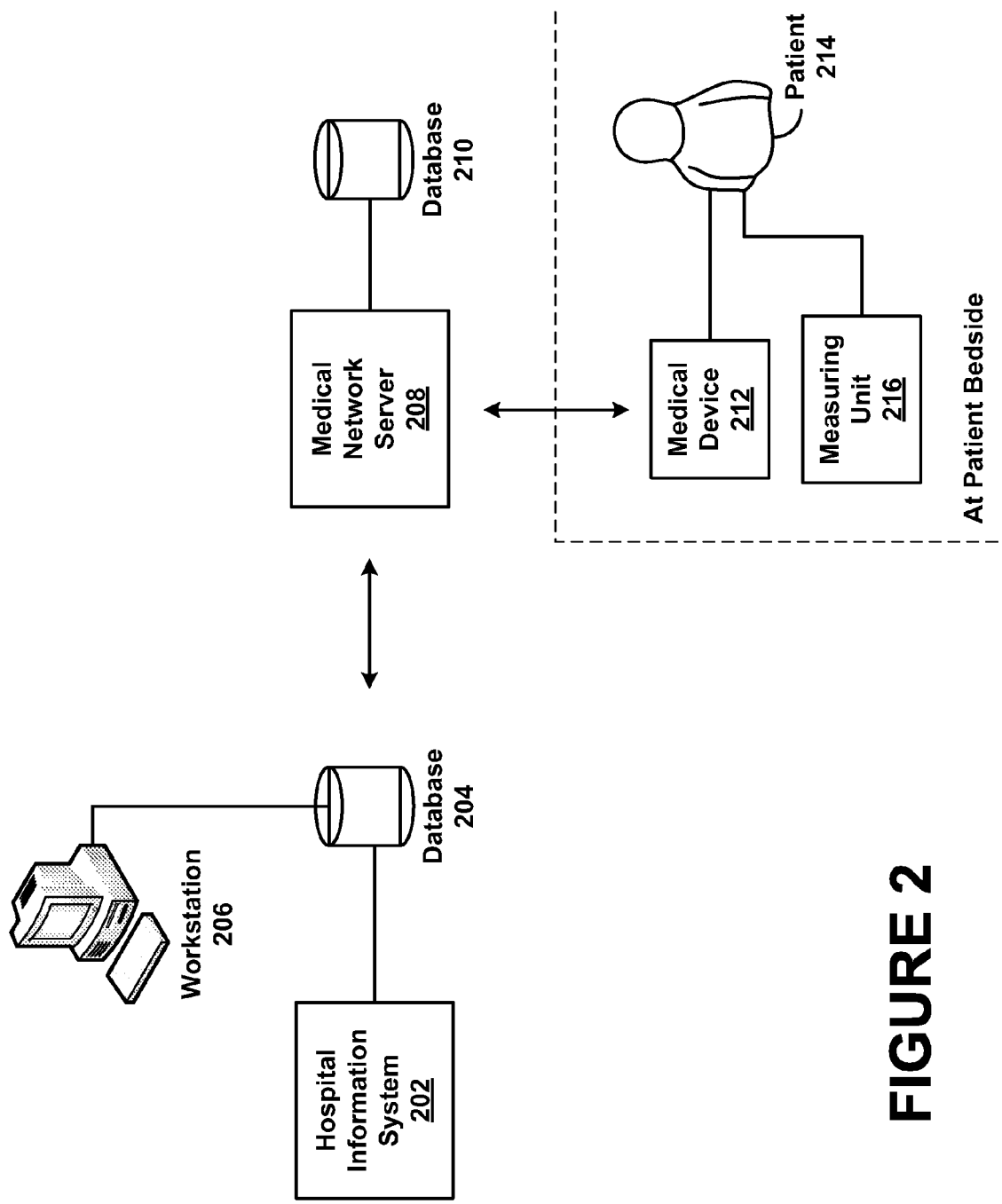
FIG. 2 illustrates another example configuration for managing and delivering patient therapy through drug delivery systems.

FIG. 2 illustrates another example configuration for managing and delivering patient therapy through drug delivery systems. In this configuration, a hospital information system 202 is connected to a database 204, and a workstation 206 may also be connected to the database 204 in a manner similar to that described with respect to FIG. 1. The hospital information system 202, the database 204, and the workstation 206 may be located at the hospital or off-site as well and connected through a network, for example.

A medical network server 208 may be connected to the database 204 to access and receive patient-specific data, CCA information, or other information useful for hospital personnel. The medical network server 208 may also be connected to a database 210. The medical network server 208 and the database 210 may be located at the hospital, remote from the patient's bedside, in the patient's room, or off-site as well.

A medical device 212 is also provided to deliver drug therapy to a patient 214. The medical device may be in communication with the medical network server 212 to receive drug library information, and to send patient demographics, status, and event information to the medical network server 212, for example. In one example, the medical device 212 may be an infusion pump as described above. A measuring unit 216 can be provided as described above as well.

The medical network server 208 may support transfer of configuration parameters from either of the databases 204 or 210 to the medical device 212. The medical network server 208 may aggregate all data related to and used by the medical device 212 to populate the databases 204 or 210. For example, patient-centric data, CCA-centric data, and event log reporting may be provided through the medical network server 208 as will generation of subcutaneous insulin dosing orders.

Figure 3:
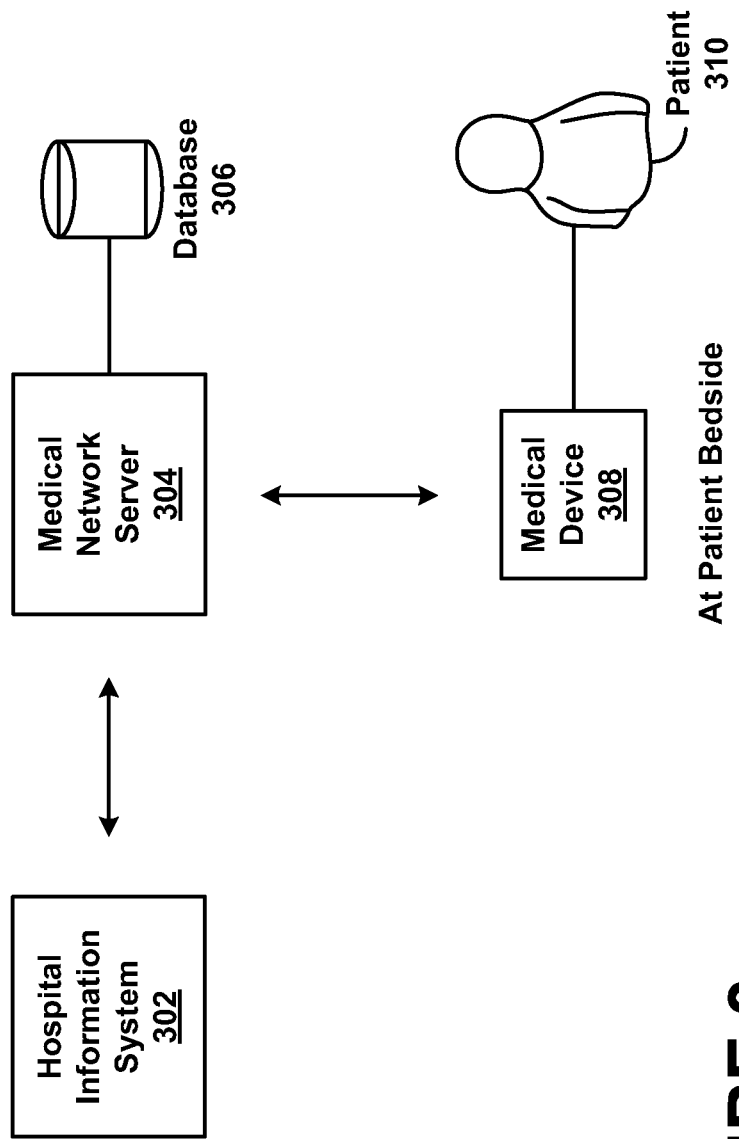
FIG. 3 illustrates yet another example configuration for managing and delivering patient therapy through drug delivery systems.

FIG. 3 illustrates yet another example configuration for managing and delivering patient therapy through drug delivery systems. In this configuration, a hospital information system 302 is connected to a medical network server 304, similar to the configuration in FIG. 2. However, only one database 306 is provided connected to the medical network server 304. A medical device 308 communicates with the medical network server 304 to deliver drug therapy to a patient 310. The medical device 308 may operate similar to the medical devices of FIG. 1 or 2, for example. The configuration as shown in FIG. 3 may also include a measuring unit (not shown) connected to the patient and in communication with the medical device 308 and/or the medical network server 304, for example.

In any of the configurations of FIG. 1, 2, or 3, a medical device administers drug therapy to a patient, and can communicate with servers and databases to send and receive patient-specific information, drug delivery information, or event logs, for example.

Figure 4:
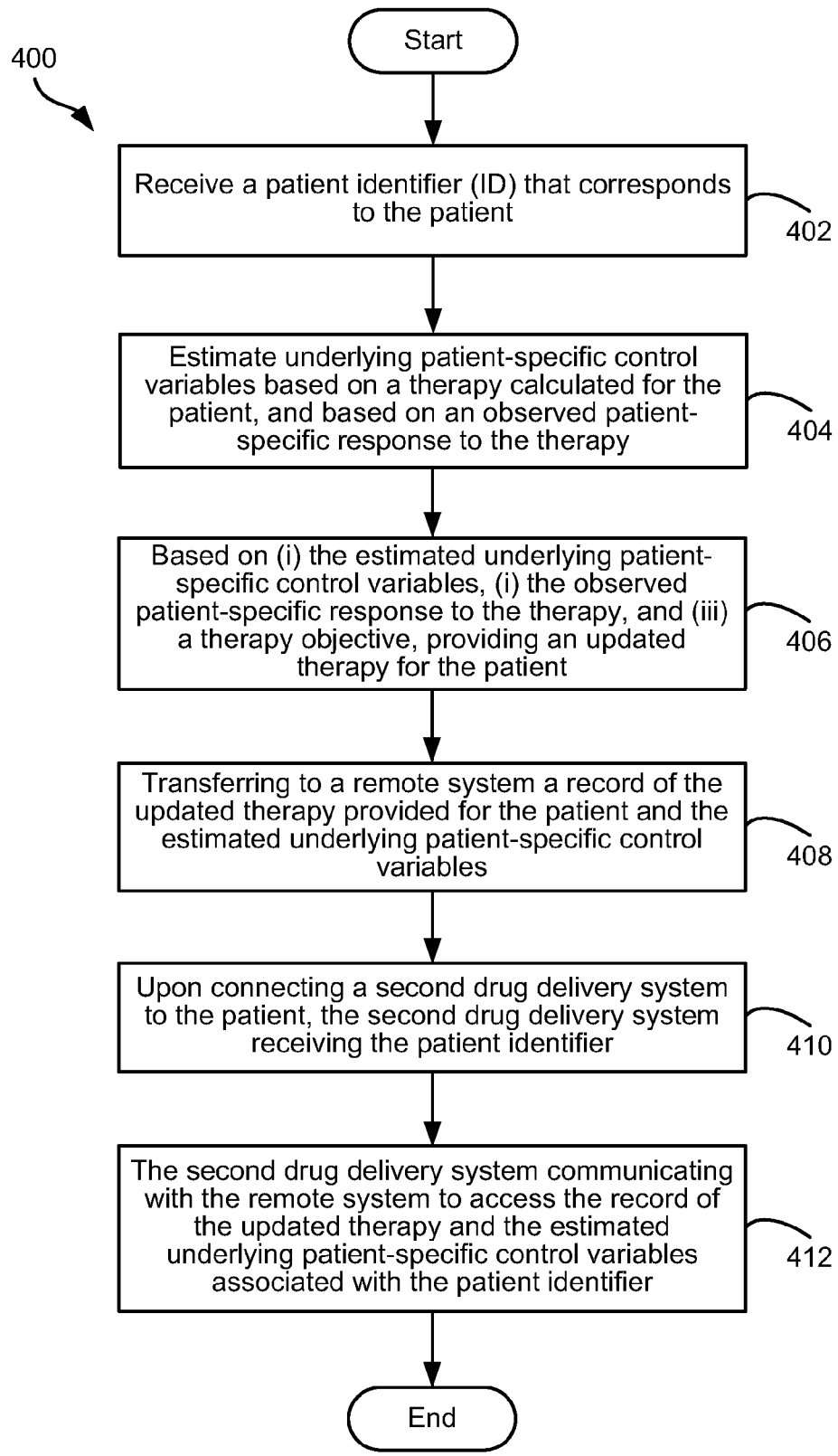
FIG. 4 illustrates an example method for delivering drug therapy using a medical device.

Referring back to FIG. 1, the medical device 108 is operated to control drug delivery to the patient 110. The medical device 108 may be connected to the patient via intravenous lines, for example. FIG. 4 illustrates an example method for delivering drug therapy using the medical device 108.

Initially, as shown at block 402, the medical device 108 may receive a patient identifier (ID) that corresponds to the patient. The patient ID may be included on a bracelet on a patient that may be received by scanning the bracelet, for example. The medical device 108 can then use the patient ID to retrieve patient-specific information from the database 104 or hospital information system 102.

The medical device 108 can then initiate the drug therapy to the patient 110. To do so, as shown at block 404, the medical device can estimate underlying patient-specific control variables (e.g., blood glucose levels) based on a therapy calculated for the patient 110, and based on an observed (i.e., measured) patient-specific response to the therapy. The therapy may be calculated depending on all patient-specific variables, such as height, weight, etc., and an appropriate treatment is determined for the patient's condition.

Because the medical device 108 observes a response of the patient to the therapy, the medical device 108 can update the therapy to better address the needs of the patient. Thus, as shown at block 406, based on the estimated underlying patient-specific control variables, the observed patient-specific response to the therapy, and a therapy objective, the medical device 108 provides an updated therapy for the patient.

The medical device 108 will continue to monitor and observe the patient response to the therapy to continually update the therapy as needed. The medical device 108 may transfer to a remote system, such as the database 104 for example, a record of the updated therapy provided for the patient and the estimated underlying patient-specific control variables, as shown at block 408. The therapy information transferred from the medical device 108 to the database 104 may also include the measured patient responses and the times at which the measurements were taken. Of course, the measurement data can also be transferred directly from the measuring unit 114 to the database 104. Thus, the updated therapy information can be stored on an alternate device for backup, or to transfer control of the therapy to another device. For example, upon connecting a second drug delivery system to the patient, the second drug delivery system may receive the patient identifier, as shown at block 410, and the second drug delivery system may communicate with the remote system to access the record of the updated therapy and the estimated underlying patient-specific control variables associated with the patient identifier, as shown at block 412. The second drug delivery system may then continue therapy to the patient. If the medical device 108 is subsequently disconnected from the patient, the second drug delivery system may continue the therapy at a point at which the medical device left off. In this manner, the therapy does not have to be restarted from an initial starting point, but rather, the second drug delivery system may use the information gathered by the first medical device 108 to maintain and continue the updated therapy.

Figure 5:
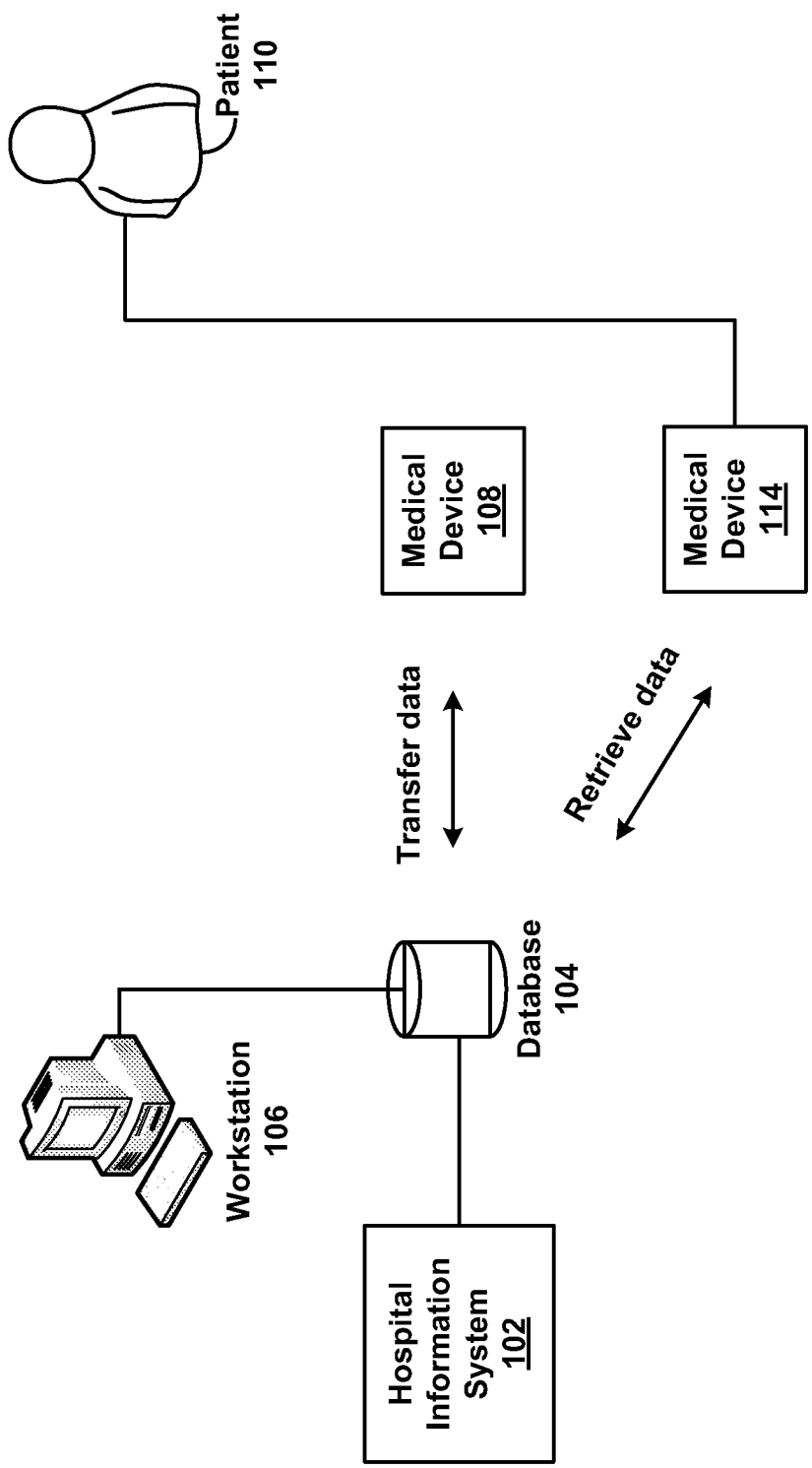
FIG. 5 illustrates one example of a configuration for transferring data from one medical device to another.

FIG. 5 illustrates one example of a configuration for transferring data from one medical device to another. As explained with reference to the method 400 of FIG. 4, the medical device 108 may transfer the updated therapy and estimated underlying patient-specific control variables to the database 104. Before, during, or after connecting a second medical device 114 to the patient 110, the second medical device 114 can retrieve the updated therapy and estimated underlying patient-specific control variables from the database 104 to continue the therapy.

Figure 6:
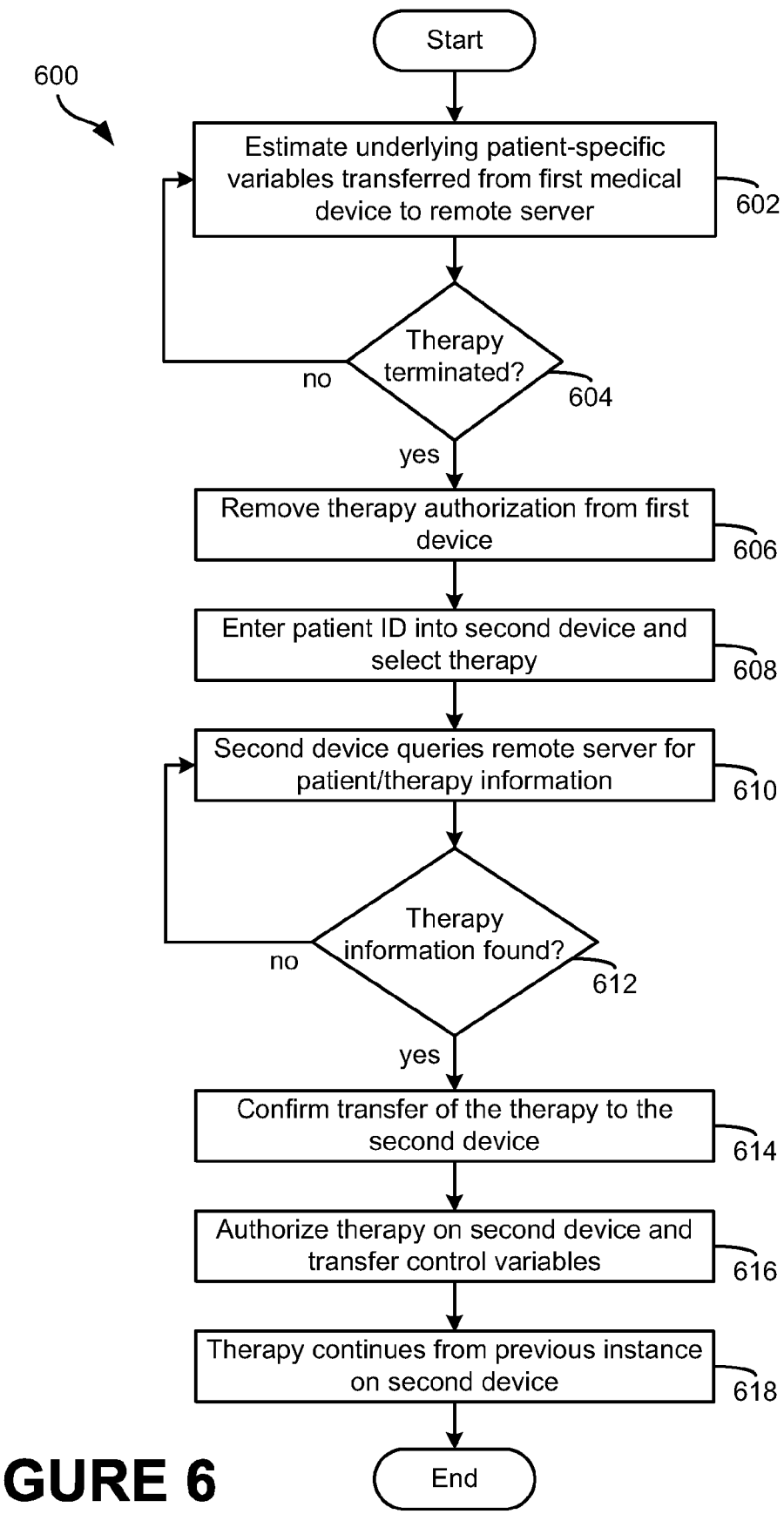
FIG. 6 illustrates another example of a method for transferring data from one medical device to another.

FIG. 6 illustrates another example of a method for transferring data from one medical device to another. Initially, as shown at block 602, underlying patient-specific control variables are estimated using a first medical device, and are transferred to a remote server. The estimated underlying patient-specific control variables may be transferred on an on-going basis, or at a specific status or log reporting point, or upon termination of therapy by the first medical device, for example. Once therapy provided by the first medical device is terminated, as shown at block 604, therapy authorization is removed from the first device, as shown at block 606. For example, a server may send a control message to the first medical device instructing the first medical device to discontinue therapy to the patient.

A second medical device may receive the patient ID in order to continue therapy to the patient, as shown at block 608. A nurse may connect the second medical device to the patient, and may enter the patient's ID and select the therapy for treatment. The second device may then query a medical network server (e.g., remote server) for the estimated underlying patient-specific control variables, as shown at block 610. If the estimated underlying patient-specific control variables are found on the remote medical network server or a database connected thereto, as shown at block 612, the information is transferred to the second medical device via a wireless or wired interface.

Transfer of the therapy data is confirmed at the second device, as shown at block 614. For example, the second device may send a confirmation signal to the medical network server indicating receipt of the data, or a nurse may manually confirm receipt of the data on the second device. The medical network server will then authorize therapy to begin using the second device, and the medical network server will transfer the control variables to the second device, as shown at block 616. Subsequently, the therapy may resume and continue from the previous instance using the second device, as shown at block 618.

It may be desirable to transfer administration of therapy from one medical device to another in many situations. For example, in a hospital setting, a patient may be transferred between rooms, and each room may include a different medical device. In order to continue feedback related treatment within a second hospital room, data collected by a first medical device is transferred to a second medical device in the second hospital room so as to resume treatment at the point left off. Thus, in an instance where a patient is transferred from an intensive care unit (ICU) to a general wing of hospital/surgery and therapy is to be continued, it may be desirable to setup a pump in the second room before switching to use of the second pump. Therapy may only be administered by one pump at any given time; however, the data can be transferred to the second pump to initiate a setup procedure or to place the second pump on standby, for example. In this manner, patient care is independent of location or a specific device, and continuity of care can be maintained.

Further, it may be desirable to transfer therapy data from one medical device to another in instances in which the therapy depends on data that is continually updated in an iterative or recursive fashion. Thus, if the therapy began at an initial stage using a first medical device and was conducted for a few days, the therapy will have changed over time based on the patient's response to the therapy. If the patient is subsequently moved to another room and transferred to a second medical device, it would be beneficial to transfer the data as well so as to continue, resume, or recalculate the therapy using the updated data rather than to restart the therapy at the initial stage.

Finally, it may be desirable to transfer therapy data from one medical device to another in instances in which a new but related therapy is provided on the new device that is dependent upon the therapy delivered through the first device. For example, the first device may be used to deliver IV medications for a particular therapy while the second device continues the same therapy but with a different drug delivery route. As a specific example, an intravenous insulin delivery pump can be replaced with a subcutaneous insulin pump just prior to discharging the patient from the hospital.

Depending on a type of therapy being provided to the patient, the data being transferred from a first medical device to a second medical device may include many common variables and patient-specific variables. Such common variables may include a therapy identification, such as for example, glucose management, heparin management, fluid management, pain management, sepsis resuscitation, cardiovascular control, etc. Other common variables include a patient identifier or medical record number (MRN), pump identification information, a date and time, and a therapy state such as an infusion status (insulin infusion dose) and a patient response (last glucose level). Still other common variables may include a system clock or timing of therapy administered and measurements taken.

Estimated patient-specific control variables that may be transferred from a first medical device to a second medical device may include such information as an estimated insulin sensitivity $S_i$, an estimated insulin basal delivery rate (BR) (a rate of continuous insulin supply needed for such purposes as controlling cellular glucose and amino acid uptake), estimated feedback gains, estimated model parameters, estimated insulin clearance rate $P_i$, estimated endogenous glucose production, and estimated saturation terms. More information may be transferred depending on a type of therapy being provided, and examples of additional information may include any of the variables found within any of Equations (1)-(9) described below.

In example methods, algorithms and adaptive controllers are used with patient variables to learn a patient response to therapy to personalize therapy decisions and enable dosing recommendations. A medical device may be operated using a software system that manages and delivers patient therapy in a manner to learn estimated patient-specific control variables.

The control variables represent a model of the patient's response to the particular medication and are calculated over time. For example, two variables can be calculated recursively on a time series of glucose measurements and infusion rates. As the calculated control parameters converge to optimal values, a quality of glucose management improves.

In one example therapy, a set of control variables, pV, provides information for managing glucose in the future based upon an observed history of insulin readings, glucose concentrations, and related therapy events. For example, an estimated insulin, pV.SI, and an endogenous glucose clearance, pV.PG, enable future estimation and control of glucose concentration. Alternately, patient variables can include estimated glomerular filtration rate (GFR), background or basal infusion rate, and additional multiplication factors for non-linear dosing terms.

The process of learning the patient variables may be time consuming and costly because the process is performed on the basis of diagnostic information in combination with drug infusion information. There are direct expenses related to diagnostic measurements as well as indirect costs associated with clinician workflow and patient discomfort. Additionally, information content of the data collected can be limited by the drug response time and frequency of measurements. For example, in the case of glucose management, a patient's glucose profile over time is often recorded on the basis of painful and inconvenient blood draws. This time series of diagnostic values and the recorded infused insulin is used to calculate the patient variables.

Because the process of collecting and processing patient-specific variables can be costly, both in terms of time and pain to a patient, it would be useful to transfer such information from a first medical device to a second medical device when treatment is to be continued on the second medical device, for example.

Below are example models that used patient-specific variables to treat patients. Many other models exist depending on a therapy being provided to a patient, for example.

EXAMPLE 1

Autoregressive Moving with Exogenous Inputs Model (ARX) Defining the Patient-Specific Control Parameters Used with Model-Predictive Control In the case of glucose management, it is beneficial to develop an empirical model of the patient's glucose response to insulin therapy because the model can be used to determine an optimal insulin infusion dose. The model describes how a current glucose measurement is related to prior glucose concentrations and an insulin that has been infused, and the model is parameterized in a manner that is specific to the patient receiving treatment. More particularly, in one example, an autoregressive with exogenous inputs (ARX) model is used to represent a particular patient's response to insulin therapy via the equation:

$$\hat{g}_t = \sum_{i=1}^{p} \alpha_i g_{t-i} + \sum_{i=1}^{q} \beta_i u_{t-i} \qquad \text{Equation (1)}$$

where $\hat{g}_t$ is a estimated glucose concentration at time t, $g_t$ is a measured glucose concentration at time t, $u_t$ is an infused insulin at time t, p represents the total number of $\alpha_i$ autoregressive parameters, q is the total number of exogenous input terms, and $\alpha_i$ and $\beta_i$ are patient specific underlying control parameters associated with an ith prior glucose measurement and insulin dose respectively. In this example the model parameters, $\alpha_i$ and $\beta_i$ are selected to enable a calculation of the patient glucose at time t, $\hat{g}_t$, based upon a history of p prior glucose measurements and q prior insulin doses, Alternately, the equation above can be written:

$$\hat{g}_t = \theta_t^T \phi_t \qquad \text{Equation (2)}$$

where $\theta_t$ is the vector of parameters $\alpha_i$ and $\beta_i$ at time t, T is the transpose operator and $\phi_t$ is the vector of prior glucose measurements and insulin doses. Specifically, $$\theta_t = [\alpha_{t-1} \alpha_{t-2} \ldots \alpha_{t-p} \beta_{t-1} \beta_{t-2} \ldots \beta_{t-q}]^T$$

and $$\phi_t = [g_{t-1} g_{t-2} \ldots g_{t-p} u_{t-1} u_{t-2} \ldots u_{t-q}]^T,$$

At each time, t, $\theta_t$ is updated using a recursive least squares estimator:

$$\theta_t = \theta_{t-1} + \eta e_t K_t \qquad \text{Equation (3)}$$

$$K_t = \frac{P_{t-1} \phi_t}{\lambda + \phi_t^T P_{t-1} \phi_t}$$

$$P_t = \frac{1}{\lambda}(I - K_t \phi_t) P_{t-1}$$

where $\lambda$ is a (positive constant) forgetting factor that represents the memory horizon of the update algorithm, K is a gain matrix, P is a covariance matrix, I is the unity matrix, $\phi_t$ is defined above, $\eta$ is a step size of the update equation for $\theta_t$, and $e_t$ is the error between the observed $g_t$ and estimated glucose concentration.

Hence, at each point in time, the underlying patient specific control parameters, $\theta_t$, are adapted to the patient receiving therapy until the model is able to accurately predict the patient's future glucose response to a particular insulin therapy. For example, $\theta_t$ is updated based on the step size and the observed error $e_t$ until such point in time where $\theta_t$ at a present time substantially equals the previous $\theta_t$ measurement, or is within an acceptable error amount.

In time, the model as expressed in Equations (1)-(3) becomes more accurate as the model is personalized to the patient and provides an optimal estimate of blood glucose through time and in the future for the patient.

The model as shown in Equations (1)-(3) can be used in a model predictive controller or other well-known model based adaptive control scheme to determine an optimal insulin input. Fundamentally, a quality of an insulin recommendation may be directly related to the quality of the model and the accuracy of the recursively estimated parameters, $\theta_t$.

Given a beneficial value of patient-specific control variables and a cost of calculating the variables, decision support applications provided through an infusion pump interface can record a set of patient variables to a file, database, or memory location. When the infusion device is replaced, the process of re-calculating the patient-specific control variables does not have to be re-initiated if the patient-specific control variables are transferred to a second device.

The patient-specific characteristics related to therapies can be represented through a patient-specific control variable set that can be used by a replacement infusion device without losing information that is beneficial to target therapy.

A patient connected to a first infusion system receiving therapy is provided a patient therapy record including at least a patient identifier (ID), such as a medical record number (MRN) and calculated patient-specific control variables, such as GFR, glucose clearance, insulin utilization constants, saturation terms, and variables as described above in Equations (1)-(3), for example. A patient therapy record includes additional variables, such as, measurement frequency, recommended therapy decisions, glucose measurements and associated samples times, infusion rates and associated adjustment times, patient weight, patient gender, patient diabetes type, patient serum creatinine level, patient steroid use, patient age, patient events, and times related to data elements, for example.

Figure 7:
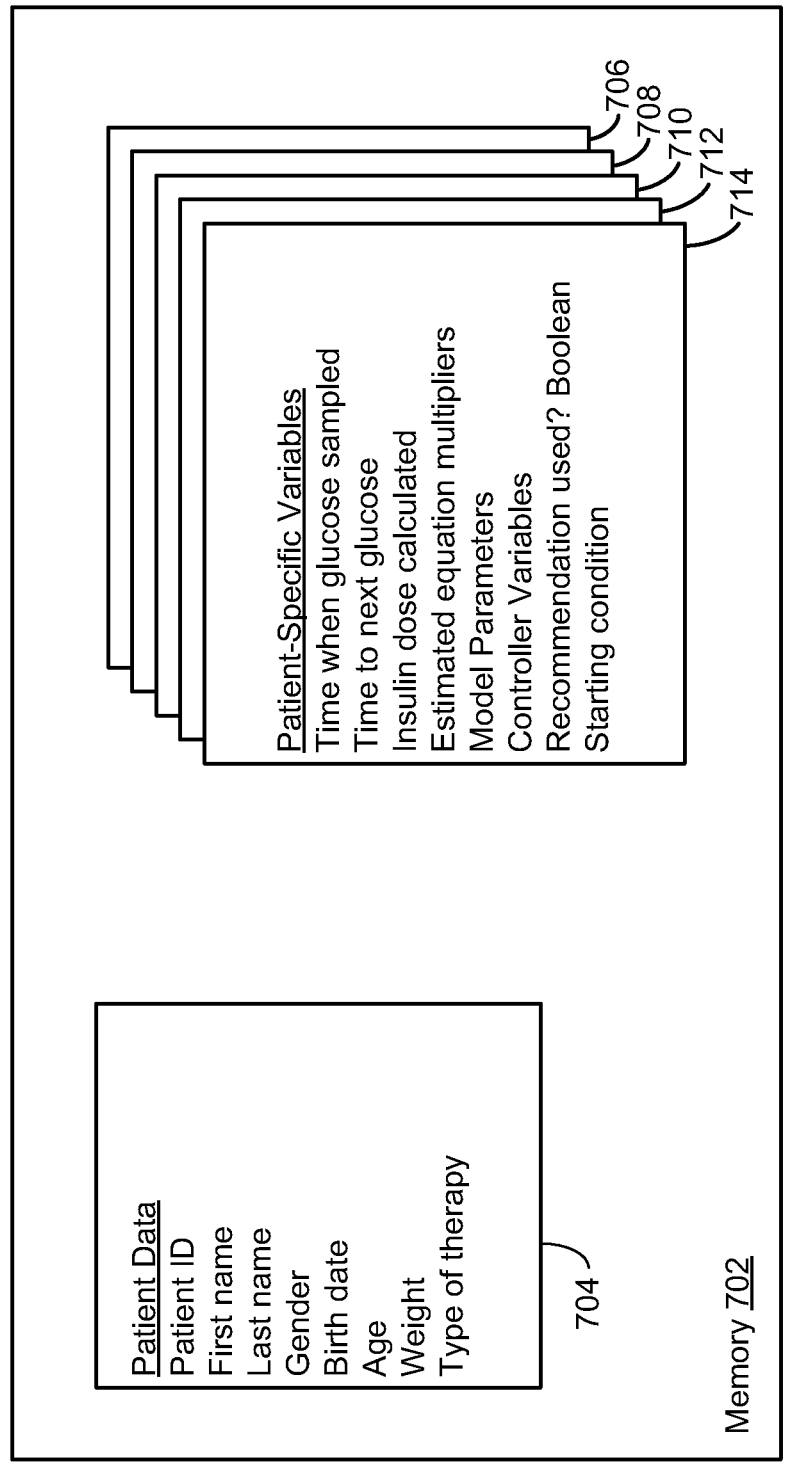
FIG. 7 illustrates one example of a memory for storing a patient data record and patient-specific variable records.

FIG. 7 illustrates one example of a memory 702 for storing a patient data record 704 and patient-specific variable records 706-714. The memory 702 may be included within any number of devices, such as a hospital information system, a server, a database, or a medical device, for example.

As mentioned above, the patient data record 704 includes the patient ID, and other information relating to characteristics of the patient. The patient-specific variable records 706-714 include information specific to a patient based on the patient's response over time to therapy being provided. The memory 702 may store new patient-specific variables 706-714 at predetermined time intervals (to store the patient's updated response), and each subsequent record may include updated information. For example, the record 714 may include current patient-specific variables and the records 712-706 may include progressively older patient-specific variables.

The calculated patient-specific control variables provide a basis for personalization of the therapy to the individual, and are therefore recorded. Although the example above is specific to glucose management, it is recognized that control variables, such as model parameters, that are calculated on the basis of a patient's data represent information that is patient specific and can be used to personalize almost any therapy at the bedside.

On an ongoing and periodic basis, the patient-specific variable records 706-714 may be transferred to a remote system and recorded in a database. The most current patient-specific variable record 714 may be transferred at each transfer period, or the previous N patient-specific variable records 706-714 may be transferred at each transfer period. In the example illustrated, N=5, but N can be tailored to meet the needs of the particular patient model algorithm. Transfer can occur in time increments that approach continuous communication or periodically on a minute-by-minute basis. In addition, transfer can be asymmetric and occur in conjunction with therapy updates.

For example, when a therapy is confirmed on medical device, the medical device may send patient demographic information and patient specific variable records to the remote server. Whenever therapy is adjusted, the same or updated information (e.g., new glucose measurements) is sent to the remote server. The data can be sent as an XML encoded message using wireless or wired communication interface to a remote system, for example.

If the patient-specific variable records 706-714 are stored on a medical device administering the therapy to a patient, the medical device may transfer the records 706-714 to a server or to another medical device, for example. The medical device may store a new patient-specific variable record at predetermined time intervals, and may maintain storage of all patient-specific variable records collected. However, when performing a transfer of the patient-specific variable records to a server, the medical device may only transfer the five most recent patient-specific variable records 706-714 to the server, for example, so as to send the previous five glucose readings, basal rates, etc., to the server or another medical device so that therapy can be resumed/continued at a point where therapy was discontinued using the first medical device.

The records 706-714 may be recorded as a single data unit and transferred remotely at specific intervals or divided into normalized components that are transferred when updates or changes occurred. However, the remote transfer of the patient-specific variable records enables an ongoing representation of the calculated patient-specific control variables to be saved for use by other systems and other devices.

The records 706-714 may be transferred by the medical device to a server, or from the server to a medical device using any number of data transfer protocols. For example, the records 706-714 may be transferred using the user datagram protocol (UDP), the transmission control protocol (TCP), the file transfer protocol (FTP), or other proprietary protocols as desired. Further, the records 706-714 may be transferred using any number of wired or wireless techniques, and thus, the medical device or server may include a wired or wireless interface (e.g., receiver/transmitter) to perform the transfer of data.

Prior to or after disconnecting a first infusion device from the patient, a user can initiate a stop command followed by a transfer of the current patient-specific variable record to the remote system, for example. However, the first infusion device may loose power or fail for unknown reasons. Consequently, frequent updates of changing patient-specific variables may be performed to insure proper backup and record of patient therapy information.

After a transfer of the patient-specific variable records 706-714, a first infusion device can be disconnected from the patient and replaced by a second device. A clinician provides the patient identifier to the second device. This can be accomplished through manual entry of a medical record number, a bar code scanner, or a radio frequency identifier (RFID). Alternately, a biometric identification metric can be used to associate the second device with a particular patient identifier. The second device can access the remote system and identify prior therapies associated with the patient. The second device then displays a selection of available therapies associated with recorded patient variable records. Alternately, after identifying the patient, the user selects the desired therapy.

The second device queries the remote system, identifies the associated patient control variable(s), and asks the user to confirm initialization using previously estimated therapy control variables. The second device may also provide information regarding a time the patient control variable(s) was last updated to ensure the therapy information is sufficiently recent, for example.

Upon confirmation, the patient-specific variable records 706-714 are transferred from the remote system to the second device and are used to begin therapy at the point where therapy was previously discontinued on the first device.

If the patient therapy control variable(s) is not found or unavailable, the system provides a means for manual entry of specific patient variables that can be obtained from the remote system interface.

Recognizing that a transfer from one infusion system to another involves interruption of the therapy, an optional safety feature enabling a reduction in recommended or automatically infused drug can also be provided. The process involves determining the time that therapy was interrupted, a time limit, and a reduction rule that may or may not consider the total time of interruption. For example, in the case of glucose management, a therapy interruption greater than 30 minutes may produce an automatic reduction of infused insulin by 80%.

EXAMPLE 2

Dosing Equation with Patient-Specific Control Parameters

A glucose dosing calculator may take the form of:

$$I_t = f(t, g_t, \tilde{I}_{t-1}, \overline{\theta}_t, \overline{G}) \quad \text{Equation (4)}$$

where t is the time, $I_t$ is a calculated insulin dose at time t, $\tilde{I}_{t-1}$ is a delivered insulin dose over the previous time period, $g_t$ is a glucose measurement at time t, $\overline{\theta}_t$ is a vector of calculated underlying patient-specific control parameters, $\overline{G}$ is a set of target glucose concentrations, and $f$ is a function that maps or translates the parameters into a recommended insulin dose. The parameter vector $\bar{\theta}_t$ may be referred to as underlying patient-specific control variables or parameters. The control parameters enable determination of a patient specific insulin dose because the control parameters are calculated on the basis of an observed glucose response to insulin dosing.

More specifically, the function $f$ of Equation (4) can be defined and the calculation of $I_t$ can be performed on the basis of the following nonlinear equation:

$$I_t = M_1(g_t - G) + M_2(g_t - G)^2 \quad \text{Equation (5)}$$

where $I_t$ is greater than zero, and $M_1$, $M_2$ are multiplication constants estimated over time on the basis of error between an observed and desired glucose response to insulin dosing. In essence, $M_1$ and $M_2$ are underlying patient-specific control parameters or elements of $\bar{\theta}_t$. The method of calculating the underlying patient-specific control variables can be performed using a recursive least squares estimator, a Bayes estimator, or control rules based upon a level and change of patient glucose concentration over time, for example.

As an example, the method of calculating the underlying patient-specific control variables can be performed using established methods of parameter estimation, such as extended Kalman filtering, recursive least squares estimation, Bayesian estimation, or proportional control rules that are used to adjust $M_1$ and $M_2$ on the basis of a calculated error, such as a difference between observed and expected glucose concentrations. For example, see Goodwin and Sin, *Adaptive Filtering, Prediction and Control,* 1984, the entire contents of which are incorporated herein by reference.

As a specific illustrative example, under the assumption that the partial derivative of an observed glucose concentration with respect to a calculated insulin rate is negative (i.e., glucose levels decreases with increased insulin), a pseudo gradient descent algorithm can be used to determine $M_1$ and $M_2$ on the basis of a difference between observed and desired glucose readings. For example, given the error:

$$e_t = \bar{g}_t - g_t \quad \text{Equation (6)}$$

where $\bar{g}_t$ is a desired or target glucose concentration at time t, the parameters $M_1$ and $M_2$ are updated according to the following:

$$M_1 = M_1 - \alpha \cdot e_t$$

$$M_2 = M_2 - \beta \cdot e_t \quad \text{Equation (7)}$$

where $\alpha$ and $\beta$ are tunable positive constants. At each measurement, estimated underlying control variables are updated according to Equation (5) and, in time, become personalized to the insulin-glucose response of the patient.

Figure 8:
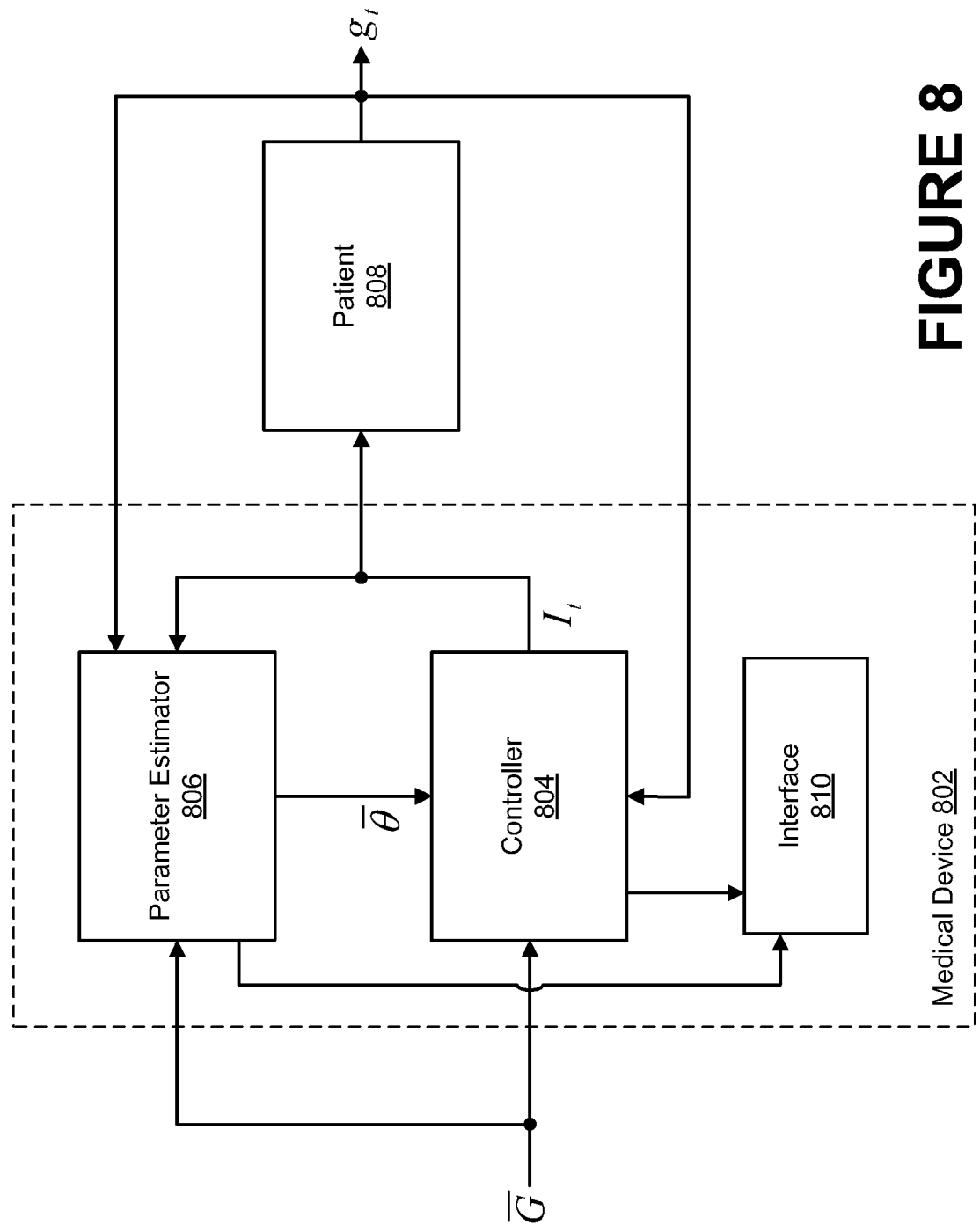
FIG. 8 illustrates a block diagram including an example medical device with an integrated on-board controller for modeling a patient's response to therapy and calculating the underlying patient-specific control variables.

FIG. 8 illustrates a block diagram including an example medical device 802 for calculating the underlying patient-specific control variables. The medical device 802 includes a controller 804 and a parameter estimator 806. The medical device 802 is connected to a patient 808. The medical device 802 further includes an interface 810, which may be a wired or wireless interface to communicate with other network devices, for example.

In operation, a target response to therapy is determined and a corresponding set of target glucose concentrations, $\bar{G}$, is selected by the physician or medical director. For example, the target therapy may be selected as about 120 mg/dL or in the range of about 100 to about 150 mg/dL. The set of target glucose concentrations, $\bar{G}$, is provided to the controller 804 and the parameter estimator 806. In addition, the controller 804 and the parameter estimator 806 receive the glucose measurement at time t, $g_t$, as recorded from the patient 808. The parameter estimator 806 outputs a vector of calculated underlying patient-specific control parameters, $\bar{\theta}_t$, to the controller 804. In turn, the controller 804 outputs the calculated insulin dose at time t, $\tilde{I}_{t-1}$, calculated according to any of Equations (4)-(7) above, to the parameter estimator 806 and administers the calculated insulin dose to the patient 808.

The controller 804 and the parameter estimator 806 may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, the controller 804 and the parameter estimator 806 may represent circuitry that is wired to perform the specific logical functions in the process, or a processor for executing the specific logical functions. Alternative implementations are included within the scope of the example embodiments of the present application in which functions may be executed out of order from that shown or discussed, including substantially concurrent or in reverse order, depending on the functionality involved, as would be understood by those reasonably skilled in the art.

The medical device 802 may store any of the underlying patient-specific control variables $\tilde{I}_{t-1}$, $g_t$, $\bar{\theta}_t$, and $\bar{G}$ in memory (not shown). The medical device 802 can then transfer any of this data to a server or other medical device using the interface 810, for example.

EXAMPLE 3

Pharmaco-Kinetic Pharmaco-Dynamic (PK-PD) Model with Patient-Specific Control Parameters Used with a Self-Tuning Regulator to Achieve a Target Activated Partial Thromboplastin Time (aPTT) Range Heparin is used for treatment and prevention of arterial and venous thromboembolic disease, such as deep venous thrombosis, pulmonary embolism, stroke, and ischemic heart disease. In addition, Heparin is an anticoagulant frequently associated with medication errors. A treatment objective is to provide therapeutic interference with a patient's clotting mechanism to prevent or treat thrombosis or embolism. Although therapy is common within the acute care environment, dosing of anti-coagulants, and in particular unfractionated heparin, is complicated due to patient-to-patient differences in drug efficacy, variation over time, impact of interference, and increase risks associated with sub and supra-therapeutic treatment conditions.

As a result, an anticoagulation effect of unfractionated heparin can be monitored via activated partial thromboplastin time (aPTT), which is determined via laboratory analysis following a blood draw. A dose of unfractionated heparin can then be adjusted to achieve a target clotting time on the basis of protocols that increase or decrease an infusion rate based upon a difference between observed and targeted aPTT. However, commonly used nomograms provide relatively poor therapy outcomes with studies reporting as low as 40% of all patient aPTTs in therapeutic range, for example.

An alternate method for determining a dose of unfractionated heparin may be to calculate a patient-specific response to the drug on the basis of known PK-PD models that have been adjusted to represent the patient. For example, a system including a control algorithm for modeling a patient's response to unfractionated heparin on the basis of automated aPTT readings and making adjustments is presented in "*Automated Heparin-Delivery System to Control Activated Partial Thromboplastin Time: Evaluation in Normal Volunteers*," by Cannon, C., J. Dingemanse, C. Kleinbloesem, T. Jannett, K. Curry and C. Valcke, *Circulation* 1999; 99; 751-756, the entire contents of which are incorporated herein by reference. Such a system may improve patient safety and enable clinicians to achieve therapeutic aPTT levels faster than traditional weight-based nomograms by employing an adaptive controller to rapidly personalize therapy decisions based upon how the patient responds to heparin administration. In addition, elements of the heparin management cycle can be automated to reduce clinician workload as well as the potential for medication errors.

Using methods and systems disclosed herein enables transfer of aPTT readings from a centralized laboratory to an infusion system equipped with an advanced controller for recommending changes to unfractionated heparin dosing. Specifically, after receiving a notification of a new lab value, the infusion system algorithm may calculate an updated unfractionated heparin infusion rate and provide an alert if clinician intervention is necessary.

If the aPTT value is within therapeutic range, an alert is not sent because immediate action by the nurse may not be necessary. If the lab value is out of range (i.e., the lab value ranges can also be stored in the drug library), an alarm is issued. Thus, the systems disclosed herein provide a centralized server for managing patient data or estimated underlying patient-specific control parameters, and provide for automatic transfer of personalized therapy from one device to another, for example.

In addition to providing a recommended rate for heparin infusion, the infusion device may display a time for a next blood draw and aPTT analysis. Clinicians are reminded at designated times through a user interface and/or remote notification system to check a patient's blood aPTT level so that an updated heparin infusion rate can be determined by the algorithm. A series of escalating alarms are generated if a heparin measurement is not received in the designated time.

The estimated underlying patient-specific control variables are calculated via a feedback controller that is embedded in the infusion system. After the initial dosing calculation, the algorithm functions as a feedback controller by providing bolus and/or continuous heparin infusion updates and a time for a next aPTT reading based on the history of differences between the aPTT readings and the target range. When coagulation times are less than a targeted range, the heparin infusion rate is increased. Conversely, coagulation times greater than desired times result in a decrease in a recommended heparin infusion rate. Once the aPTT reading is in the therapeutic range, the heparin infusion rate is unchanged and the time between aPTT measurements is increased to 24 hours.

Initial dosing is provided on the basis of the patient's age, weight, gender, smoking history, and serum creatinine level, for example. A multivariate initial dosing algorithm, based upon a priori population PK-PD analysis, is optimized to achieve a near-therapeutic response within 6 hours according to the particular treatment modality. Subsequent readings are used to update calculated underlying patient-specific control variables associated with a PK-PD model of heparin dynamics using either a Bayesian optimization algorithm, extended Kalman filter, or other parameter estimation technique.

The PK-PD model relates the aPTT response to heparin and underlying patient-specific control parameters, $\bar{\theta}$, through the following equations:

$$\frac{dR(t)}{dt} = -\left[\lambda + \frac{a_1}{a_2 + R(t)}\right]R(t) + \frac{S_u}{V_d}u(t) \quad \text{Equation (8)}$$

$$R(t) = \log(aPTT(t)) - \log(aPTT_o)$$

$$\bar{\theta} = \begin{bmatrix} \lambda & a_1 & a_2 & \frac{S_u}{V_d} \end{bmatrix}$$

where $R(t)$ is the modeled aPTT response to heparin administration, $aPTT_o$ is the baseline aPTT measurement, $S_u$, is the drug sensitivity to heparin, $a_1$ and $a_2$ are constants associated with the saturable mechanism of elimination of heparin, $\lambda$ is the elimination rate constant, $u(t)$ is the heparin infusion rate, and $V_d$ is the volume of distribution.

With the addition of each new aPTT measurement from the laboratory information system, $\bar{\theta}$ is updated via Bayesian or other estimation techniques such that $R(t)$ more closely matches the observations.

Finally, $\bar{\theta}$ is utilized to adjust the heparin infusion rate through model predictive control in which the aPTT prediction, $R(t+\tau)$ where t is the current time and $\tau>0$, is used to determine the optimum recommended infusion rate.

At each update point, the control parameters, $\bar{\theta}$, together with the history of aPTT observations, heparin infusions, patient identification information, and time indices may be transferred from the infusion device to the remote system and recorded in an SQL database, for example. Such information may also be transferred at other points in time as well. This information constitutes an information record to resume therapy on another infusion device should the current device fail or require replacement, for example. Further, the information can be transferred directly to another medical device to start or resume therapy using the other medical device.

EXAMPLE 4

Computer-Directed Blood Glucose Delivery Algorithm

Intravenous insulin is a method of diabetes management, and methods for administering the insulin may be complex and limited to intensive care units. A computer-directed algorithm for advice on delivery of intravenous insulin that is flexible in blood glucose timing and advises insulin dosing in a graduated manner may be used to maintain glycemic control. An intravenous insulin protocol includes the formula:

Insulin dose/hr=(blood glucose−60)×(multiplier)   Equation (9)

Studies have shown that a multiplier starting at about 0.02 provides desired results. The multiplier can be progressively modified until the insulin dosing formula controls glucose within a targeted range.

To initiate the method, a blood glucose value measurement is taken and entered into a medical device, and an initial insulin infusion rate is calculated according to Equation (9), with the multiplier set at about 0.02. Based on a rate of change to the glucose level, the medical device may notify the nurse when the next blood glucose value is needed (e.g., between about 20 to about 120 minutes). For example, for an initial blood glucose level of 295 mg/dl, a multiplier of 0.02 indicates an initial insulin rate of 4.7 units/hr. If a second blood glucose level decreases to 256 mg/dl (e.g., less than 15%), the multiplier may be increased by 25% to increase the insulin dose to 4.9 units/hr. If subsequent serially measured blood glucose levels decrease satisfactorily (e.g., 205 mg/dl followed by 3.6 units/hr, 168 mg/dl followed by 2.7 units/hr, and 115 mg/dl followed by 1.5 units/hr) until the blood glucose level is less than a low target value (e.g., 69 mg/dl followed by 0.2 units/hr), then at that time, the multiplier is shifted downward and the next two blood glucose levels and insulin doses (e.g., 98 mg/dl followed by 0.8 units/hr and 110 mg/dl followed by 1 unit/hr) may be centered in a target range.

A high target for blood glucose level may be between about 120 to about 140 mg/dl, and a low target may be between about 80 to about 100 mg/dl. Within Equation (9), the multiplier may be initiated at about 0.01 to about 0.02, and a maximal duration of time between glucose measurements is about 120 minutes. A frequency of blood glucose monitoring is set at an interval predicted to prevent a blood glucose level from dropping below about 60 mg/dl, for example. When blood glucose values are stable, the interval between blood glucose level monitoring will be increased to the preset maximum interval.

As shown by the example above, it may take multiple blood glucose measurements and a considerable amount of time before a multiplier is found to achieve a target blood glucose level. The multiplier is thus a patient specific underlying control variable that may be determined over time, and can be transferred between medical devices to maintain continuous service to a patient without having to restart an insulin therapy from initial values, for example. Further, the previous multipliers, blood glucose measurements, and insulin dose rates form a history of therapy provided to the patient and may also present valuable information to the medical device administering therapy to the patient. Thus, such historical information may also be transferred between medical devices to maintain continuous service to the patient without having to restart an insulin therapy from initial values, for example.

Methods, devices, and systems disclosed herein provide a manner for utilizing patient-specific control variables associated with one therapy for diagnostic purposes or for alternate and related therapies. The methods provide a semi-automated manner for therapeutic decisions in which risk level is mitigated.

Any of the servers or medical devices described herein may include or have functions performed by a module, a segment, or a portion of program code, which includes one or more instructions executable by a processor for implementing specific logical functions or steps in the process. The program code may be stored on any type of computer readable medium, for example, such as a storage device including a disk or hard drive. In addition, the servers or medical devices described herein may include circuitry that is wired to perform the specific logical functions in the process, or a processor for executing the specific logical functions. Alternative implementations are included within the scope of the example embodiments of the present application in which functions may be executed out of order from that shown or discussed, including substantially concurrent or in reverse order, depending on the functionality involved, as would be understood by those reasonably skilled in the art.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method for managing and delivering patient therapy through electronic drug delivery systems, the method comprising:
a first electronic drug delivery system that is connected to a patient receiving a patient identifier that corresponds to the patient;
the first electronic drug delivery system estimating underlying patient-specific control variables based on (i) a therapy provided for a patient and (ii) an observed patient-specific response to the therapy, wherein the underlying patient-specific control variables include values of parameters for an algorithm executed over time to determine dosages;
based on (i) the estimated underlying patient-specific control variables, (ii) the observed patient-specific response to the therapy, and (iii) a therapy objective, the first electronic drug delivery system providing an updated therapy for the patient based on updated underlying patient-specific control variables so as to adapt the therapy to the patient;
the first electronic drug delivery system transferring to a remote system a record of the updated therapy provided for the patient and the updated underlying patient-specific control variables;
upon connecting a second electronic drug delivery system to the patient, the second electronic drug delivery system receiving the patient identifier;
the second electronic drug delivery system communicating with the remote system to access the record of the updated therapy and the updated underlying patient-specific control variables associated with the patient identifier;
determining a time that therapy was discontinued by the first electronic drug delivery system and based on the time an amount at which to adjust the therapy being provided; and
adjusting the record of the updated therapy to take into account the amount at which to adjust the therapy that will be provided by the second electronic drug delivery system.

2. The method of claim 1, wherein the first electronic drug delivery system is an infusion system.

3. The method of claim 1, wherein the underlying patient-specific control variables are selected from a group consisting of insulin sensitivity, glomerular filtration rate (GFR), basal infusion rate, multiplication factors, insulin clearance, insulin utilization constants, saturation terms, drug sensitivity, renal function, and drug clearance rates.

4. The method of claim 1, further comprising the first electronic drug delivery system transferring to the remote system the record of the updated therapy provided for the patient and the estimated underlying patient-specific control variables on a periodic basis.

5. The method of claim 1, further comprising the first electronic drug delivery system transferring to the remote system the record of the updated therapy provided for the patient and the estimated underlying patient-specific control variables at least at each instance of a change in one of the estimated underlying patient-specific control variables.

6. The method of claim 1, further comprising receiving a stop command at the first electronic drug delivery system that indicates to discontinue therapy to the patient and responsively transferring current estimated underlying patient-specific control variables and the record of the updated therapy to the remote system prior to the first electronic drug delivery system being disconnected from the patient.

7. The method of claim 1, further comprising the second electronic drug delivery system receiving the record of therapy and the updated underlying patient-specific control variables associated with the patient identifier from the remote system and continuing the therapy for the patient at a point where the therapy was previously discontinued by the first electronic drug delivery system.

8. The method of claim 1, wherein the first electronic drug delivery system wirelessly transfers to the remote system the record of the updated therapy provided for the patient and the estimated underlying patient-specific control variables.

9. The method of claim 1, further comprising removing therapy authorization from the first electronic drug delivery system after the first electronic drug delivery system transfers to the remote system the record of the updated therapy provided for the patient and the updated underlying patient-specific control variables.

10. The method of claim 1, further comprising the first electronic drug delivery system storing (i) the record of the updated therapy provided for the patient and (ii) the estimated underlying patient-specific control variables on a periodic basis.

11. The method of claim 1, wherein the therapy provided for the patient is based on a function in the form of $I_t = f(t, g_t, \tilde{I}_{t-1}, \bar{\theta}_t, \bar{G})$, where t is the time, $I_t$ is a calculated insulin dose at time t, $\tilde{I}_{t-1}$ is a delivered insulin dose over a previous time period, $g_t$ is a glucose measurement at time t, $\bar{\theta}_t$ is a vector of estimated underlying patient-specific control variables, and $\bar{G}$ is a set of target glucose concentrations.

12. The method of claim 1, wherein the therapy provided for the patient includes dosing of anti-coagulants including unfractionated heparin, and wherein the observed patient-specific response to the therapy includes an anticoagulation effect of unfractionated heparin monitored via activated partial thromboplastin time (aPTT).

13. The method of claim 12, wherein the updated therapy includes adjustments to a dose of unfractionated heparin to achieve a target clotting time based on observed and targeted aPTT.

14. The method of claim 12, wherein the underlying patient-specific control variables are selected from a group consisting of heparin infusion updates, a time for a next aPTT reading, a drug sensitivity to heparin, or a level of saturable mechanism of elimination of heparin.

15. The system of claim 1, wherein the first drug delivery system wirelessly transfers to the remote system the record of the updated therapy provided for the patient and the estimated underlying patient-specific control variables.

16. A system for managing and delivering patient therapy through drug delivery systems, the system comprising:
a first drug delivery system connected to a patient and receiving a patient identifier that corresponds to the patient, and based on (i) estimated underlying patient-specific control variables, (ii) an observed patient-specific response to the therapy, and (iii) a therapy objective, the first drug delivery system providing an updated therapy for the patient based on updated underlying patient-specific control variables so as to adapt the therapy to the patient, wherein the underlying patient-specific control variables include values of parameters for an algorithm executed over time to determine dosages, and the first drug delivery system transferring to a remote system a record of the updated therapy provided for the patient and the updated underlying patient-specific control variables; and
a second drug delivery system receiving the patient identifier and communicating with the remote system to access the record of the updated therapy and the updated underlying patient-specific control variables associated with the patient identifier, wherein the second drug delivery system is further configured to determine a time that therapy was discontinued by the first electronic drug delivery system and based on the time an amount at which to adjust the therapy being provided, and to adjust the record of the updated therapy to take into account the amount at which to adjust the therapy that will be provided by the second electronic drug delivery system.

17. The system of claim 16, wherein the first drug delivery system and the second drug delivery system are infusion systems.

18. The system of claim 17, wherein the second drug delivery system receives the record of therapy and the updated underlying patient-specific control variables associated with the patient identifier from the remote system and continues the therapy for the patient at a point where the therapy was previously discontinued by the first drug delivery system.

19. A computer readable medium having stored therein instructions executable by a computing device to cause the computing device to perform the functions of:
receiving from a first electronic drug delivery system a record of estimated underlying patient-specific control variables for a patient, the underlying patient-specific control variables being based on (i) a therapy provided for a patient and (ii) an observed patient-specific response to the therapy, wherein the underlying patient-specific control variables include values of parameters for an algorithm executed over time to determine dosages;
receiving from the first electronic drug delivery system an updated therapy provided for the patient based on updated underlying patient-specific control variables so as to adapt the therapy to the patient, the updated therapy being based on (i) the estimated underlying patient-specific control variables, (ii) the observed patient-specific response to the therapy, and (iii) a therapy objective;
transferring to a second electronic drug delivery system a record of the updated therapy provided for the patient and the updated underlying patient-specific control variables associated with the patient;
determining a time that therapy was discontinued by the first electronic drug delivery system and based on the time an amount at which to adjust the therapy being provided; and
adjusting the record of the updated therapy to take into account the amount at which to adjust the therapy that will be provided by the second electronic drug delivery system.

* * * * *